(12) United States Patent
Da Silva

(10) Patent No.: US 6,913,929 B1
(45) Date of Patent: Jul. 5, 2005

(54) SEXUAL FIDELITY AND SEX CRIME VERIFICATION

(75) Inventor: Luiz B. Da Silva, Danville, CA (US)

(73) Assignee: Pearl Technology Holdings, LLC, Livermore, CA (US)

( * ) Notice: Subject to any disclaimer, the term of this patent is extended or adjusted under 35 U.S.C. 154(b) by 0 days.

(21) Appl. No.: 09/551,281

(22) Filed: Apr. 18, 2000

(51) Int. Cl.⁷ .............................................. G01N 33/48
(52) U.S. Cl. ...................... 436/63; 436/166; 436/174; 436/177; 436/94; 422/58; 422/61
(58) Field of Search .................. 422/58, 61; 436/164, 436/166, 169, 173, 174, 175, 177, 63, 94–95

(56) References Cited

U.S. PATENT DOCUMENTS 4,334,540 A * 6/1982 Preti et al. .................. 600/300
4,503,143 A * 3/1985 Gerber et al. ............... 435/7.36
5,032,501 A * 7/1991 Milner ........................... 435/6

OTHER PUBLICATIONS

Turvey, "A–Utopic Determination of Oral Sex in Forensic Sciences", Knowledge Solutions Library, Jun. 1995.*
Checkmate, internet, copyright 1999–2003.*

* cited by examiner

Primary Examiner—Lyle A. Alexander
(74) Attorney, Agent, or Firm—John P. Wooldridge

(57) ABSTRACT

A series of unique biochemical tests are combined to enable unskilled law enforcement and private investigation personnel to rapidly perform sex crime investigations on skin swipes and body fluid residues deposited on specific articles of clothing. The invention also allows spouses to privately identify and monitor infidelity activities of their mate through the application of this test kit to personal clothing and other areas where body fluids may be found.

8 Claims, 2 Drawing Sheets

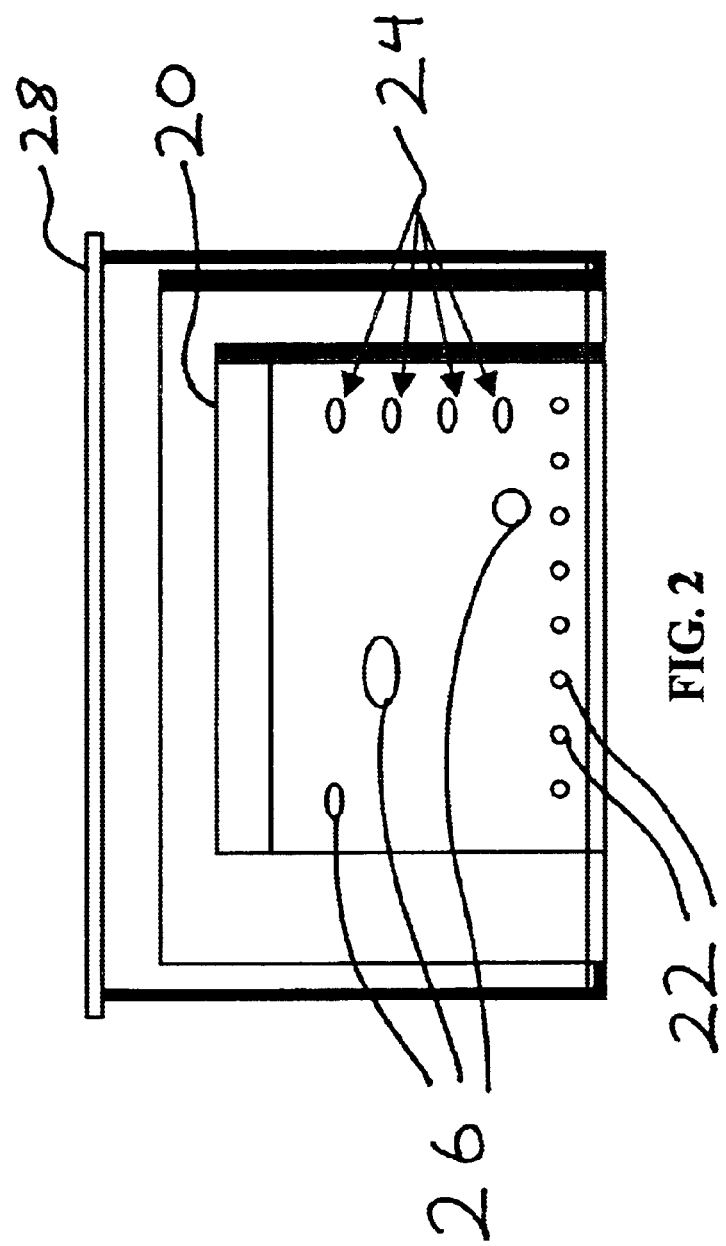

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 1
gaaaaaggag ccaacaaaat                    20

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 2
attttgttgg cccctttttc                                              20
```

SEXUAL FIDELITY AND SEX CRIME VERIFICATION

BACKGROUND OF THE INVENTION

1. Field of the Invention

The present invention relates the detection of intimate contact between individuals and more specifically, it relates to new biochemical tests that can be applied to human body fluid and residue-material left on clothing and skin that signify sexual contact between two individuals.

2. Description of Related Art

Rape in all forms, infidelity, and molestation are serious human aberrations that are well documented in the literature throughout the world. Most rape investigations focus on the collection of semen and isolation of DNA for a genotype match to a suspect. In cases where no semen is identified, the investigation can become clouded in uncertainty and resolution of the facts of the case can become problematic. Hard evidence is often difficult to obtain when a male is infertile. However, the seminal fluid does have specific enzymes that can point to ejaculation without the presence of sperm. When vaginal penetration is not accomplished, molestation and fondling are even harder to document in the laboratory. The detection of foreign body-fluids, cellular debris and fibers greatly aid the investigation.

In cases of suspected infidelity, one mate may desire methods to perform forensic investigations without the knowledge of the other mate. However, a well-equipped forensic laboratory is not available to the general public.

When infidelity is implicated, certain forensic identifiers are possible depending upon the type of sexual contact. Intimate human contact between a male and female can encompass four types of interaction: (1) touching and stroking of the hair and the skin over the surface of the body, (2) probing mucous membranes either digitally or orally over parts of the body including the sex organs, (3) vaginal penetration either orally, digitally, or during the act of sexual intercourse, and (4) rectal exploration or penetration. In addition, semen and individual sperm cells, as well as blood can be carried to all parts of the partner's body during prolonged sexual activity. Further chemical exposures can result during the sexual encounter from spermicides and foams, lubricants, rubber vulcanizing agents from condoms, and other materials available to the participants.

All these human interactions transfer unique biochemical compounds between individuals. If these biochemicals can be identified a considerable amount of forensic information can be obtained. It is well documented during the forensic investigation of rape cases that sperm cells can be collected, DNA fragments isolated and amplified using specific DNA primers and the polymerase chain reaction (PCR), the DNA fragments separated by electrophoretic methods, and unique DNA bands compared to suspects. This technique has been used to conclusively identify the responsible male. Other clues on the female such as hairs and fibers have been used to place the male in close proximity to the assaulted female.

Although considerable effort has been placed on identifying the male, seldom has sexual contact with a female been identified through unique chemical marker compounds transferred to the male. Indicator compounds such as the color of a specific lipstick or unique perfumes transferred to clothing have been ascribed as forensic tools. However, female body-fluid markers or other biochemical indicators on the male have not been addressed during a forensic investigation. Observation and research now point to new tools that can advance sex crime investigations or infidelity tests performed by spouses.

Many "suspect" males have limited options for washing the possible incriminating compounds from the penis following the sexual encounter. In some situations, complete showering may be available. Fortunately, the base of the penis and scrotum have rugal folds that may escape all but thorough cleansing. Thus, incriminating compounds deposited during vaginal penetration or following oral sex may rest in the folds of the scrotum, inner thighs and attendant hairs.

Therefore, a need exists for the identification chemicals associated with sexual contact between individuals. In particular target compounds need to be identified in forensic investigation of sex crimes and those individual who seek information concerning potential sexual liaisons of their mate with other individuals. In particular a complete field forensic combination analysis (tests) is needed that allows unskilled individuals to perform chemical analyses for target compounds derived during a sexual encounter.

SUMMARY OF THE INVENTION

It is an object of the present invention to provide a battery of tests for determining whether sexual contact between individuals has occurred.

It is another object of the present invention to provide such tests that may be performed in a timely manner and allow decisions to be made by criminal investigators or by a spouse concerned with the fidelity of their mate.

Still another object of the invention is to provide a convenient combination analytical and biochemistry test battery to identify target compounds indicative of intimate sexual contact between individuals. These target compounds may be taken, e.g., from clothing or hygiene products for target compounds indicative of sexual contact between individuals.

A further object of this invention is to provide multiple combination tests for the determination of a sexual contact between individuals. Multiple tests will reduce the likelihood of false positive results.

The invention provides a series of unique biochemical tests that may be combined to enable unskilled law enforcement and private investigation personnel to rapidly perform sex crime investigations on skin swipes and body fluid residues deposited on specific articles of clothing. The invention also allows spouses to privately identify and monitor infidelity activities of their mate via personal clothing and other areas where body fluids may be found.

There are five suites of chemical signature-compounds that can be transferred to the male during a sexual encounter with a female. These would include: (1) oral-derived saliva compounds (2) blood transferred due to menstruation or trauma, (3) vaginal compounds, (4) compounds derived from the lower colon, and (5) industrial chemicals derived from lubricants, condom products, and spermicidal agents and foams.

Oral-derived compounds include ultratrace levels of amylase, proteins, and acids from the cheek cells, lips, and saliva from the female or male. Chemicals such as dimethylfuran, di- and tri-methyl sulfides and other compounds are indicative of saliva and diagnostic of intimate human contact if found on the genitalia of the male or assaulted victim.

Blood from a female can contain unique DNA markers that point to female XX-chromosomes. In addition, mitochondrial DNA from a female is specific. These DNA markers are well characterized by standard laboratory polymerase chain reaction (PCR) protocols and antibody tests and can be utilized for the identification of intimate female contact with a male.

The odor of vaginal secretions contain compounds such as acetic acid, pyridine, furfural, benzaldehyde, short chain fatty acid, 3-hydroxy-butanone, and other unique compounds.

Lower colon marker compounds contain considerable amounts of the breakdown products of red blood cells. The characteristic odor of fecal material has been characterized and appears to be solely derived from indoles.

The identification of spermicidal agents would be very indicative of possible sexual contact between a male and female. Thus, the identification of lubricants, spermicides or rubber-related compounds would be very indicative of a sexual involvement.

Following a sexual encounter, the undergarments or underwear of both individuals are a rich source of bio-material and other evidence. This evidence could allow a criminal investigator or spouse to know whether a suspect or sexual partner had sex within about 48 hours with another person. The close proximity of the genitals to the underwear allows the chemical resting on or within the organs to leach out onto the moistened underwear. Thus, all of the above described materials can show up in the underwear.

Various areas of the body and materials placed upon the sex organs and materials coming from the sex organs can be characterized by various testing methods. Underwear and undergarments would be a logical source of materials for testing due to the aforementioned reasons, but these tests may be performed on other articles as well.

BRIEF DESCRIPTION OF THE DRAWINGS

FIG. 2 illustrates the analysis of sex crimes and infidelity through the use of thin layer chromatography.

DETAILED DESCRIPTION OF THE INVENTION

Figure 1:
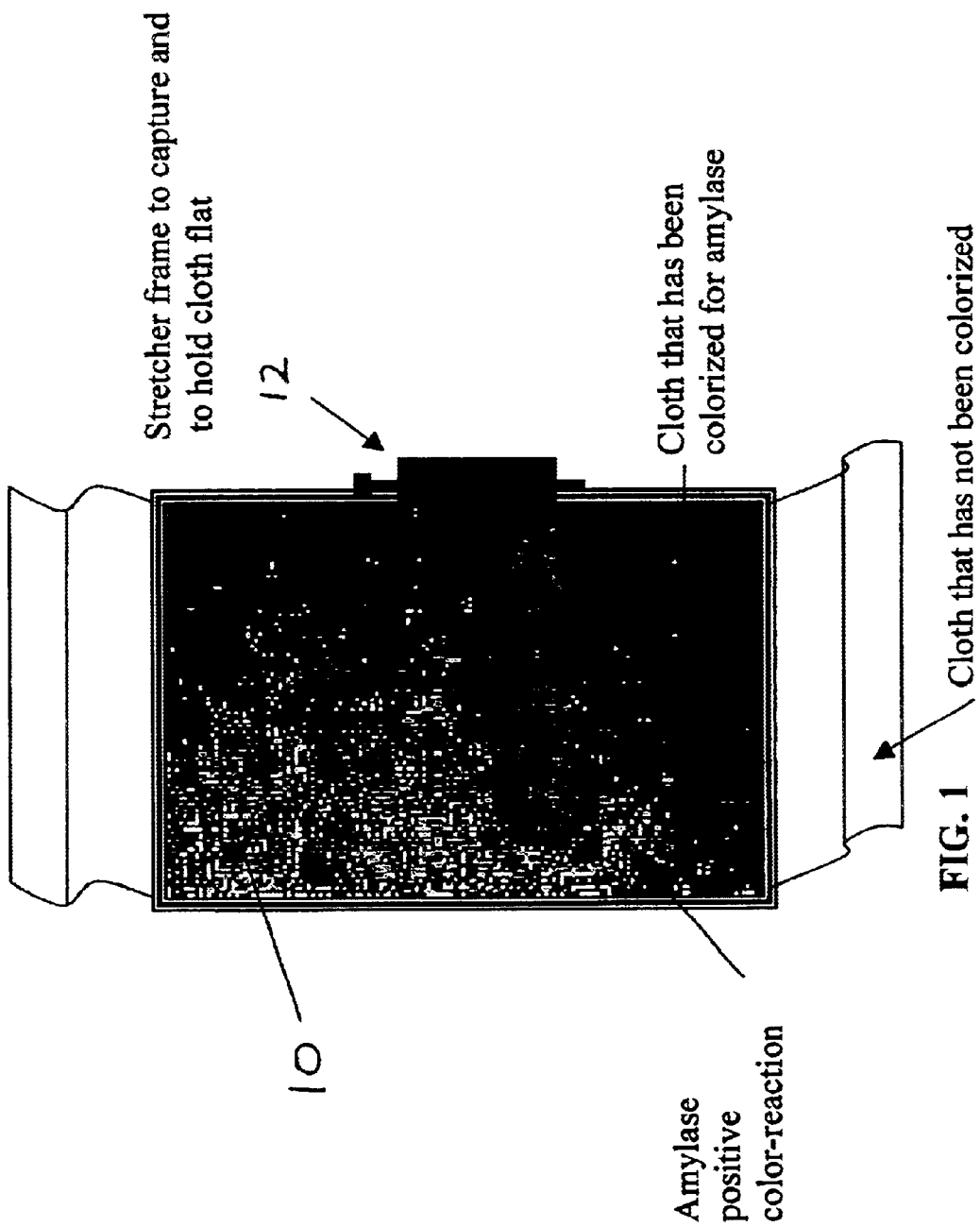
FIG. 1 shows a small section of suspect material clamped between a cloth spreader for use in performing an amylase test.

Body fluids, transferred to skin and clothing from vaginal mucus membranes, semen, saliva, the lower colon, and industrial chemicals, leave unique identifier molecules that can now be identified during forensic investigations. A series of unique biochemical tests are combined to enable unskilled law enforcement and private investigation personnel to rapidly perform sex crime investigations on skin swipes and body fluid residues deposited on specific articles of clothing. The invention also allows spouses to privately identify and monitor infidelity activities of their mate through the application of this test kit to personal clothing and other areas where body fluids may be found.

General Description

There are five suites of chemical signature-compounds that can be transferred to the male during a sexual encounter with a female. These would include: (1) oral-derived saliva compounds (2) blood transferred due to menstruation or trauma, (3) vaginal compounds, (4) compounds derived from the lower colon, and (5) industrial chemicals derived from lubricants, condom products, and spermicidal agents and foams. Each suite of compounds are very different and clearly useful for the identification of intimate sexual activities between a male and female.

Oral-derived compounds would include ultratrace levels of amylase, proteins, and acids from the cheek cells, lips, and saliva from the female. Amylase is specific for saliva. In addition, chemicals such dimethyl-furan, di- and tri-methyl sulfides and other unique compounds are very indicative of saliva and diagnostic of intimate human contact if found on the genitalia of the male.

Blood from a female can contain unique DNA markers that point to female XX-chromosomes. In addition, mitochondrial DNA from a female is specific. Thus, these DNA markers are well characterized by standard laboratory PCR and antibody tests that can be utilized for the identification of intimate female contact with a male.

Vaginal fluids are unique. The odor of vaginal secretions contain compounds such as acetic acid, pyridine, furfural, benzaldehyde, short chain fatty acid, 3-hydroxy-butanone, and other unique compounds. The ratio of these compounds is strongly dependent upon the acid-balance of the female (varying with menses). Aliphatic female acid-producers generate in their vaginal secretion large amounts of 2-piperidone, butyric acid, isovaleric acid, propionic acid, acetic acid, and other acid compounds. Non-aliphatic acid producer females appear only to have high amounts of lactic acid in their vaginal secretions. In contrast, the "spermatous" odor of the male sperm has been identified as 1-pyrroline.

Lower colon marker compounds contain considerable amounts of the breakdown products of red blood cells. The characteristic odor of fecal material has been characterized and appears to be solely derived from indoles. These compounds are very unique and the parent compound and indole metabolites are highly odoriferous to both human and animals. Although, not absolutely diagnostic for colon penetration, the appearance of indoles on frontal underwear zones can signal concern.

Industrial compounds are the most unique of the above described compounds. The identification of spermicidal agents would be very indicative of possible sexual contact between a male and female. These spermicides are not commonly utilized for typical female hygiene and the identification of this class of compounds would be very suspicious. Thus, the identification of lubricants, spermicides or rubber-related compounds would be very indicative of a sexual involvement.

Following a sexual encounter, the undergarments or underwear of both individuals are a rich source of bio-material and other evidence. This evidence could allow a spouse to know whether his or her partner had sex within about 48 hours with another person. The close proximity of the genitals to the underwear allows the chemical resting on or within the organs to leach out onto the moistened underwear. Underwear is naturally moistened with perspiration and high humidity from the moist groin area. This environment preserves the biomarker compounds. The oily nature of tissues also traps and slowly releases target compounds into the surrounding area. Thus, all of the above described materials can show up in the underwear.

Various areas of the body and materials placed upon the sex organs and materials coming from the sex organs can be characterized by various testing methods. Underwear and undergarments would be a logical source of materials for testing, due to the aforementioned reasons, but these tests may be performed on other articles as well.

It would usually be desirable for the partner who is performing the investigation of the other partner to perform the field analysis in a controlled manner. Therefore, it would be best for the partner who is doing the investigating to abstain from sex with the partner prior to running the tests.

A typical period of abstinence could be 48 hours. The investigator could use several methods to extract the chemical information from the undergarments. These would include using an aqueous or non-aqueous solvent that would not harm the underwear, dipping the entire garment or only the frontal portion of the underwear into the solvent. A miniature wringer-like apparatus mimicking the old-fashioned clothes wringer could help remove valuable information and, in fact, cause a mechanical loosening of the bio-material or material to be investigated from the garment. The undergarment could also be sampled by cutting out the selected stained portions of the undergarment with scissors and disposing of the remainder of the undergarment altogether.

A series of tests could be run, usually three in number, to yield probabilistic determination of the fidelity tests. Clear, non-coloring solvents could be used to extract the chemical information from the undergarment. These solvents should be such that they will be released or washed easily following laundering. Solvents could be placed in glass vials, plastic cups, or other types of receptacles. Various tests can be run all together in one cup, or the solvents of different natures could be partitioned into several different cups for further testing. Additional reagents would be applied in order to bring about a calorimetric or other type of analysis to clearly indicate a positive result.

Testing a males underwear for the presence of acid phosphatase has a very high probability of false positive results. This is due to normal male discharges of significant amounts of sperm and seminal fluids. Therefore, a man does not necessarily have to have a sexual encounter in order to excrete acid phosphatase. A more valid conclusion would be reached if acid phosphatase were detected in the underwear of a woman. Significant acid phosphatase in the undergarments of a woman would more clearly point to sex with a man When contraceptives are utilized, additional tests could be performed on indicative foreign compounds. This would increase the confidence of the testing results. Additional tests for other marker compounds can center on industrial products. These would include ingredients found in:

a) KY-Plus jelly: benzoic acid, carbopol 940, methyl paraben, propylene glycol and polyethylene glycol 300;

b) Summers Eve Lubricating Jelly: propylene glycol, methyl cellulose, xanthan gum, methyl paraben,pectin, propyl paraben. Women's Health Formula: glycerine, hydroxyethyl cellulose, glucano delta lactone, chlorhexidine gluconate and methyl paraben;

c) Astro Glide: glycerine, propylene glycol, polyquaternium, methyl paraben and propyl paraben;

d) Spermicides: all contain benzalkonium chloride, nonoxynol-9 and methyl paraben, polyethylene glycol;

e) Ortho contraceptrol: nonoxynol-9 (4%), methyl paraben, propylene glycol, ascorbic acid and sodium carboxymethyl cellulose;

f) All vaginal contraceptive film and sponges contain nonoxyl-9, (28%); and g) Virtually every brand of condom has nonoxyl-9.

All industrial compounds of this type possess a clear association with sexual activity. When detected, substantial conclusions can be reached concerning the indication that a sexual act had occurred.

Therefore, from the body of available information concerning the target compounds transferred between individuals during a sexual encounter, this invention provides combinations of tests that provide definitive information concerning sexual contact between individuals. Tests materials and apparatus can screen undergarments or hygiene product remnants contaminated with either a man or women who has previously been in intimate contact with the subject sexual partner under investigation.

One version would provide the following tests:
1. Amylases color test on cloth (from saliva).
2. Pyridine (and other amines) color test.
3. Industrial compounds and spermicides identification through specific color tests or thin layer chromatography (TLC).
4. Indole-specific color tests to identify colon compounds.
5. Blood test-using specific color tests for hemoglobin (hematest)
6. XX-Female chromosome antibody test The greater the number of tests in combination causes false positive to be less problematic. For example, one may generate a positive pyridine result that indicates vaginal fluids. When this compound is identified on previously clean clothing, it would be a potential indicator of a sexual encounter. Males do not have pyridine in seminal fluids. The amylase test is indicative of saliva. Alone, if positive, both tests would lead to concern. When taken together, these two tests would provide stronger evidence of a sexual act with vaginal penetration in some form, and oral sex. The identification of spermicides, vaginal lubricants, or rubber vulcanizing agents suggest higher probabilities of a sex act. A common control could be a "clean" similar brand of undergarment or analysis of the backside of the same undergarment.

It may be desirable to provide an inexpensive, simplified, thin layer chromatography (TLC) apparatus for the identification of target compounds. The compounds are eluted up the TLC plate with solvents that are specific for the target compounds. Referring to FIG. 2, the TLC plate 20 is colored by dipping or over-spraying in a suitable colorizing reagent (e.g., bismuth subnitrate to detect pyridine) to highlight compounds indicative of a sexual encounter. Compounds that can be identified by this TLC method are spermicidal compounds (e.g., nonoxyl-9), rubber vulcanization reagents (e.g., benthiazoles from condoms), vaginal creams and lubricants, indoles (from the colon), and biochemicals in vaginal fluids. The illustration in FIG. 2 shows a TLC plate with patterns that are produced from compounds 22 taken from various parts of an undergarment. The emerging patterns resulting from the solvent are identified as standard patterns 24 and patterns 26 that vary from and are compared against the standard patterns. The TLC plate is located within an enclosed tank 28. Thin layer chromatography separates the different compounds, produces patterns that are characteristic of a particular compound and is sensitive to the nanogram level.

Specific Description

As required, detailed embodiments of the present invention are disclosed herein. However, it is to be understood that the disclosed embodiments are merely exemplary of the present invention that may be embodied in various systems. Therefore, specific details disclosed herein are not to be interpreted as limiting, but rather as a basis for the claims and as a representative basis for teaching one skilled in the art to variously practice the present invention.

1. Amylase Detection Indicative of Saliva Deposition

Saliva (from the parotid gland) possesses high concentrations of amylase to aid in the digestion of carbohydrates. Three main methods (with a great many variations of reagents) are used for the analysis for amylase. These are the saccharogenic, amyloclastic, and chromolytic methods. These methods have not been used for saliva stain-detection or for the determination of amylase on undergarments or clothing.

The saccharogenic method detects the presence of enzyme activity by generating reducing materials (e.g., glucose and maltose) from starch in the presence of amylase. These reducing sugars then attack color reagents (e.g., picrate, ferricyanide, 3,5-dinitrosalicylic acid, cupric ions, etc.), causing a color change that reveals the presence and amount of amylase. The assay method for analysis would be to first spray on clothing a solution of starch and a color reagent in a phosphate buffer solution at about pH 7.0. Heating up the material in an oven at about ~37° C.+/−2° C., or microwave for 2 minutes (or at room temperature over a period of a few hours) will reveal colored spots from the suspect stain. These colored spots point to saliva stains.

The amyloclastic method measures the decrease in starch concentration in the presence of amylase. A dilute iodide solution will form an intense blue color-complex with starch molecules. As the starch concentration is depleted by amylase, there will be less blue starch-iodine color-forming capability in the substrate. Therefore, when one observes a white spot on a blue background it can be inferred that amylase was present and has been depleted of all the available starch. A phosphate/chloride/calcium buffer solution containing a dilute solution of starch is sprayed on the test garment. It is allowed to react at a slightly elevated temperature. Next a spray containing a dilute solution of potassium or sodium iodide in water is sprayed on the same area. Where amylase is present, a white spot is seen on a blue background is indicative of saliva.

The chromolytic method uses a synthetic dye-linked amylase-sensitive substrate to test for the presence of enzyme. In the presence of amylase the dye is cleaved and a color change is immediately detected. Substrate-dye examples are thiazine-labeled starches that are water insoluble. However, dye molecules attached to a starch molecule will be attacked by amylase to generate water soluble dye compounds that wash out with water leaving a white spot on a colored background. The procedure would be to spray a slurry of the dye-labeled starch on the clothing over the spot suspected of potentially containing saliva. The cloth is then incubated at slightly elevated temperature followed by rinsing with water through the garment. White spots will be visualized against a colored background for amylase positive saliva stains. Also, careful filtering will reveal a water-soluble dye forming only when amylase is present on the garment.

Therefore, a new method for testing clothing to determine the presence of amylase from saliva, comprising a color test of the saccharogenic, amyloclastic, or chromolytic (or combinations of the three) protocol, applied to suspect cloth stained with saliva, is presented. The test characterizes a piece of cloth to be tested with visible or invisible stains by contacting the piece of cloth with chemicals that will cause color changes in the presence of amylases; and observing whether the color of said chemical has changed from its original state to a new color state revealing that the amylase activity is present and further indicating that the article (e.g., cloth) encountered saliva. The chemicals can be sprayed or the cloth dipped into a solution containing the indicator chemicals. The mixture of chemicals and amylase are warmed in either at room temperature, in an oven or microwave over a time period to increase the amylase activity, further causing a visible color change on the garment. Positive amylase test can indicate that saliva was carried orally to the sex organs and then deposited on the undergarments. Thus the test points to an oral sexual encounter.

a. Amylase Detection Protocol

Referring to FIG. 1, a small (3"×3") section of the suspect material 10 is clamped between a cloth spreader 12 (similar to a needle-point frame). This apparatus, though not essential to perform this type of color test is simple, yet has not previously been applied to saliva testing on cloth or hygiene product such as a panty liner. This allows the material to be stretched for uniform coating with indicator chemicals. Because the cloth is stretched flat a consistent color reaction is observed (as illustrated in FIG. 1 at reference number 14) where amylase has been deposited. Any one of several variations of the amylase test mixtures mentioned above (in a solution of phosphate buffer at pH 7.0) is uniformly sprayed on the suspect cloth material. A spray bottle is included in a kit containing pre-mixed chemical reagents. Alternately the cloth can be dipped into a solution of the indicator chemicals. Now wetted with a light coating of indicator chemicals the cloth is warmed to allow the amylase reaction to take place. Colors can develop spontaneously with appropriate reagents or additionally the undergarment can be oversprayed with a second chemical mixture (as outlined above) to generate spots where saliva has been deposited on the undergarment. This new method is convenient, fast (only minutes for colors to develop), and does not destroy the undergarment. Multiple strips of cloth can be cut and stretched over the frame to allow for simultaneous screening capabilities on a number of different garments. For "suspects" with colored underwear, a soluble/fluid calorimetric test may be performed. As reviewed above in the chromolytic method, a water-soluble dye can be liberated from the substrate. This dye is observed in the rinse of the undergarment.

b. Other Target Compounds Indicative of Saliva Deposition

In forensic science, the identification of a single compound often does not provide the highest level of confidence necessary to provide a match between a suspect and a crime. However, if a suite of chemical compounds can be identified the likelihood of a correlation can be more substantiated. Saliva can contain over 25 compounds. In addition to characterizing amylase, the identification of additional salivary fluid compounds on undergarments would provide higher levels of confidence during an investigation. In fact a simple solvent extraction (e.g., methanol, ethanol, etc.) of the suspect cloth followed by gas chromatography-mass spectrometry (GC-MS) analysis can be used to identify a number of important salivary compounds. Although these compounds have been identified in saliva, they have not been extracted from undergarments to reveal sex crimes or infidelity. Therefore, a mail-in testing capability can be envisioned that requires only small portions of stained material to be characterized.

c. Volatile Saliva Compound Identification

A suspect undergarment or hygiene product is dipped into a solvent (methylene chloride) to extract target compounds. The solvent is then injected into a GC-MS instrument. The suite of extracted compounds generates a unique chemical fingerprint that points to saliva. The compounds to be detected are: 1-propanol, 1-decanol, 1-dodecanol, 1-tetradecanol, 1-hexadecanol, dimethyl disulfide, dimethyl trisulfide, benzyl alcohol, 2-phenylethanol, phenol, cresol, 2-, 3-, and 4-methylpyridines, indole, skatole, diphenylamine, benzaldehyde, and dimethylfurane. The concentrations of these compounds are highly dependent upon the oral hygiene of the individual. For example, pyridine, indoles, skatole, and diphenylamine are associated with periodontal disease. The detection of individual compounds is not as diagnostic as the combined detection of amylase and the characterization (by GC-MS) of three-to-four volatile compounds from saliva. A combination test can include a container to submit selected cloth samples that can be prepared and analyzed by GC-MS in a commercial laboratory.

2. Vaginal Fluid Deposition

Many compounds can be found in vaginal secretions. Their relative concentrations vary with menses. Certain compounds are characteristic of vaginal odors and these compounds' relative concentrations also depend upon the acid or base biochemistry of the women. Many of these odors are amines, acids, alcohols, and aldehydes.

a. General Suite of Vaginal Compounds

Tampons have been used to collect vaginal secretions and through these analyses compounds have been identified that can contribute to vaginal odors. Used tampons have been extracted with a solvent and the extractable compounds characterized by CC-MS. From this initial work a new fidelity test can be envisioned. Undergarments or hygiene products can be analyzed for vaginal secretions by submitting clothing to a commercial laboratory for characterization. A chemical profile of target compounds can be identified pointing to vaginal fluid exposure.

Therefore, undergarments or hygiene products, suspected of having come in contact with vaginal secretions, could be extracted with a polar solvent (e.g., methanol, ethanol, etc.) and a small aliquot of the extract subjected to GC-MS analysis. The following compounds would be considered a fingerprint (chemical signature) for vaginal fluids from aliphatic acid producing females: pyridine, 3-hydroxy-2-butanone, maleic anhydride, acetic acid, furfural, benzaldehyde, propionic acid, isobutyric acid, propylene glycol, butyric acid, 2-isopentyl-furan, isovaleric acid, 2-methylbutyric acid, heptadecane, octadecane, nonadecane, isocaproic acid, dimethyl sulfone, phenol, p-cresol, 2-peridone, 1-tetradecanol, lactic acid, and 1-hexadecanol. All organic acids are in high concentration.

A nonacid producing woman generates a different chemical profile of volatile vaginal-fluid compounds. They would be: 3-hydroxy-2-butanone, maleic anhydride, acetic acid, furfural, benzaldehyde, propylene glycol, ethylene glycol, 2-isopentylfuran, fufuryl alcohol, phenylacetaldehyde, heptadecane, octadecane, nonadecane, dimethyl sulfone, heptanoic acid-, 1-dodecane, phenol p-cresol, 1-tetradecanol, lactic acid, and 1-hexadecanol.

All compounds listed above possess unique mass spectral data. Therefore, a GC-MS analysis of suspect clothing that generates a chemical profile with the above compounds will provide high confidence that the undergarment has come in contact with vaginal secretions. A test collection kit allowing for commercial cloth samples to be submitted would facilitate chemical profile monitoring. From these analyses fidelity monitoring can be established.

b. Amino-compounds in Vaginal Secretions

In addition to acids, aldehydes, alcohols, and sulfur containing compounds, the strong odor in both types of vaginal secretions is attributed to the mixture of these compounds and amines. Primary and secondary amines react easily with ninhydrin analogues or o-phthladehydes to generate red/purple-colored complexes and fluorescent chromophores.

Primary and secondary amino-compounds and amino acids are present in vaginal secretions. In order to detect biological fluid-exposures a solution of ninhydrin or o-phthladehyde in methanol can be sprayed on the clothing which, when moderately heated (or exposed to sunlight), forms highly visible colored-complexes. Thus, a spray kit containing amino compound coloring reagents, when sprayed on suspect's undergarments can reveal non-specific biological materials as red/purple-colored spots. These materials can be derived from vaginal fluids. They would color easily and they could point to vaginal fluid contamination (which has high amounts of amines, more so than normal dry skin). This could be a new approach to screen for sex crimes and infidelity.

c. Specific Vaginal Fluid and Compound Detection

No one single compound from vaginal fluids can be used to conclusively identify this type of exposure on clothing. Each compound alone could be derived from a logical source (i.e., sweat, saliva, food, home products, etc.). However, the formation of a unique pattern (chemical fingerprint) of compounds can provide a high degree of indicative information that may point to infidelity. Conclusions can be reached with more confidence if the chemical pattern of compounds were highly unique.

From the general list, certain compounds in vaginal fluid possess function groups that form specific color patterns when analyzed using thin layer chromatography. Acids can react with bromophenyl blue (pH indicator) to form yellow spots on a blue background. Aldehydes react with 2,4-dinitrophenylhydrazine and generate unique phenylhydrazone-colored products. Amines react with ninhydrin or o-phthaldehyde to form purple or fluorescent chromophores. Tertiary amines (e.g., trimethylamine, diethylmethylamine, etc.) react with Dragendorff's reagent or iodoplatinate to form orange or dark brown colored spots on thin layer chromatography plates. Therefore, a unique pattern of colored spots from vaginal fluids can be generated when suspect spots are analyzed by TLC and oversprayed with colorizing reagents. These colored spots are compared to a transparent template over-lay applied directly to the TLC plate to quickly aid in the identification of vaginal compounds. Thus, thin layer analysis and pattern recognition of vaginal fluid compounds, combined with specific color spray reagent, is another embodiment of this disclosure.

Spermicide Identification

Nonoxynol-9, is the most common spermicidal reagent used for contraception. It is easily identified by GC-MS analysis. Chemically nonoxynon-9, α-(4-nonylphenyl)-ω-(hydroxypoly-oxy-1,2-ethanediyl), is really a series of 4-nonylphenyl-1-polyethyleneglycol ethers that do not easily generate a color-complex with standard laboratory reagents. However, it will chromatograph on a thin layer chromatography (TLC) plate, as illustrated in FIG. 2. A convenient method to identify Nonoxynol-9 is to apply a methanol extract of suspect cloth material to a TLC-plate, elute the plate with a suitable solvent (e.g., methanol, ethanol toluene, etc.) and then stain the plate with iodine vapor to highlight all the compounds. As one example, Nonoxynol-9 will be revealed at an $R_f$ value of 0.5 with a characteristic brown-to-yellow color. Thus, TLC with subsequent colorization over-coat on the TLC plate or similar substrate will generate a unique colored band at the correct $R_f$ value to indicate that a spermicidal agent has been used. Alternately, the test can be performed in a manner similar to an "early pregnancy" test in which a colored band must be present after a predetermined time interval in an open window on the TLC apparatus. A semi-transparent over-lay template will indicate the position where the Nonoxynol-9 should appear to indicate a positive test. Thus, when this test is positive, there will be an indication that spermicide has contaminated the undergarments.

Indoles

The breakdown of red blood cells and proteins generates copious amounts of indoles. These compounds are in high concentrations in fecal material. One compounds, skatole, produces the fecal-odor. When foreign fecal material is suspected on undergarments, a color test can be performed using oxalic acid. Died paper previously saturated with oxalic acid will turn pink in the presence of indole vapors. Indoles are also easily characterized using GC-MS assays.

Female Menstrual Blood Identification

Menstrual blood contains marker compounds. Menstrual discharge contains not only blood, but also endometrial debris, catabolites, prostaglandins, enzymes, cervical mucus, desquamated vaginal epithelial cells, and bacteria. Unless bleeding is excessive, clotting is prevented by a high level of fibrinolysin from the endometrium. All these compounds can identified in the laboratory. Specific cytology staining techniques are available for tissue samples and GC-MS analysis of blood residue can reveal prostaglandins and steroids.

The simplest at-home test available would be for the detection of occult blood on undergarments. Although simple to use this method has not been applied to fidelity testing. The test is based on the principle that the peroxidase activity of blood decomposes hydrogen peroxide resulting in the oxidation of a color reagent (e.g., o-toluidine, etc.) during the liberation of oxygen. An alternative color-generating method is observed when the reagents 3,5,3',5'-tetramethylbanzidine (blue color) or phenolphthalein (pink color) come in contact with occult blood and 3% hydrogen peroxide. These color tests can be in a home test kit for blood-contaminated undergarments.

Lipstick Color Identification

Lipsticks are typically a mixture of low melting wax (saturated hydrocarbons) and dyes. Waxes are easily identified using GC-MS instrumentation. Once placed on undergarments the color of lipsticks can be identified with thin layer chromatography (TLC). A field TLC-kit for home use would have eosine (red), methylene blue, and Texas-red dyes as standards to compare against. For example, a silica gel thin layer chromatography plate will generate an $R_f$ spot for eosine at a value of 0.5 when methanol is used as the solvent system. The kit has a color chart and $R_f$ values for other lipstick dyes.

XX-Female Chromosome Test:

Determining the gender of evidentiary samples can be an important part of a forensic investigation Gender information, particularly when combined with DNA analysis, can serve to distinguish biological evidence from two individuals. Male and female chromosomes differing by the XY or XX chromosome can be measured to identify the gender of the samples. Two recent methods have been developed to look at evidentiary samples. However, these tests have not been applied to fidelity testing.

a. Fluorescence In Situ Hybridization (FISH)

The first method centers on directly staining the chromosomes in isolated cells. These labeled cells can be easily characterized under a microscope. The general approach uses a technique called Fluorescence In Situ Hybridization (FISH). This chromosome staining method has been shown to accurately detect the presence of male epithelial cells in cervicovaginal smears obtained in alleged rape cases. The FISH protocol has also been shown to identify correctly the gender of two-week old dried bloodstains.

Thus, with this background information, a new fidelity test arises. When clean undergarments are extracted (rinsed) with a buffer solution, cells may be filtered and isolated. Cells are placed on a microscope slide and then directly stained with a mixture of X- and Y-specific chromosome probes labeled with a highly fluorescent dye. X-specific Spectrum Green probe and Y-specific Spectrum Orange probe penetrate the cell walls and attach to their respective chromosome pair. The Y chromosome probe is highly specific for a specific DNA base pair sequence located in the center of the human Y-chromosome, whereas the X chromosome probe is highly specific for the short AATGG base-pair repeats in X chromosomes. Following the staining procedure, cells are rinsed to remove excess dye and easily examined under a microscope. Cells with both a green (X-chromosome) and orange (Y-chromosome) fluorescent-labeled chromosome are female. Stains are commercially available and small microscopes with sufficient resolving power to 1,200× are now very inexpensive ($10–50). However, this approach to confirm female cells on the undergarments of male subjects has not been applied to forensic and infidelity investigations.

b. Restriction Enzyme Cutting and Polymerase Chain Reaction

Enzymes are commercially available that digest DNA forming highly specific DNA fragments. These "restriction enzymes" can be selected that generate gender-specific DNA fragments. A gender assay can utilize Polymerase Chair Reaction (PCR) amplification to increase the concentration of a X- and Y-chromosome DNA fragments from highly dilute samples. These fragments are then analyzed by gel electrophoresis (EP) to reveal only a single EP-band of 106 base pairs for female or a double EP-band at 106 and 112 base pair for male X and Y chromosomes. Thus, if the analysis does not reveal a Y chromosome base pair at 112, one can infer that this sample possibly was generated from female cells. This highly specific, yet simple, forensic investigation can be carried out in most commercial laboratories that posses gel electrophoresis apparatus. Samples for fidelity testing can be collected in a home sampling kit and submitted to a commercial laboratory.

As a step further leading to a home test kit, oligonucleotide probes can be synthesized that will specifically bind to gender-specific DNA fragments. Oligonucleotide probes are known for the X chromosome (RR 29: 5'-GAAAAAGGAGCCAACAAAAT-3') and the Y chromosome (RR 28: 540 -ATTTTGTTGGCCCCTTTTTC-3'). When a fluorescent label is attached to the 3' end of these probes, a novel fidelity assay kit (similar to an early pregnancy test kit arises). It is standard DNA work to convert these labeled probes to "Dot Blot" test kits utilized for forensic investigations and much of the current-day human genome research and development and disease testing protocols.

Acid Phosphatase Test

In the event that an undergarment is suspected to be contaminated with sperm a swipe of the stain will initially involve microscopic examination for the presence of sperm cells. In addition, because of the high level of tyrosine in semen, stains fluoresce bright blue under a UV light source. This is also an easy home test for sexual assault and infidelity testing on clothing.

In the event that there is no sperm (ejaculate devoid of sperm), acid phosphatase may be detected. Commercial kits are available to screen for stains of acid phosphatase. The tests are based on the enzymatic cleavage of phosphate from dyes, naphthyl-phosphate, thymolphthalein monoposphate, etc. Other reactions, p-nitrophenylphosphate (colorless) to p-nitrophenol (yellow), are similar to alkaline phosphatase tests, but work well with stained clothing. However, they have not been correctly applied to fidelity testing.

Conclusions

Therefore, from data available a variety of fidelity tests can be performed. Some tests can be accomplished in the field, while others require laboratory testing. Below, is a summary of some of the fidelity tests discussed above.

| Target Compounds | Analysis Methods | Protocol |
| --- | --- | --- |
| Amylase | Enzymatic | Spot-color test |
| Saliva compounds | GC-MS | Volatile compounds |
| Vaginal fluids | GC-MS/TLC | Volatile compounds |
| Spermicides | GC-MS/TLC | Phenyl ethers |
| Indoles | Color/GC-MS | Volatile compounds |
| Occult blood | Enzymatic | Peroxidase/Color |
| Lipstick | TLC | $R_f$/Color |
| XX- and XY chromosomes | Hybridization | FISH and Dot Blot |
| Acid phosphatase | Color | Phenol forming |

A literature review points to amylase assays using home test-kits. Volatile compounds in saliva, vaginal fluid, indoles, and spermicides can be chemically fingerprinted using GC-MS analysis in the laboratory. Only by using GC-MS can the ratios of salivary and vaginal compounds be characterized definitively. Chemical fingerprint information can be obtained when TLC and specific colorization reagents are employed for many of the biological samples. Occult blood can be assayed using a home test-kit that focuses on blood's capacity to liberate oxygen from hydrogen peroxide. Red colors from lipsticks can be characterized easily using a TLC apparatus. Cells staining to reveal XX chromosomes would be very definitive of female contact with a male subject. This test could be performed at home. However, a test to visualize stained cells requires a small microscope. Acid phosphatase can be measured with a home kit.

Finally, antibodies that have specific affinities for human chorionic gonadotropin (hCG) proteins could be utilized to form home tests of exposed undergarments. These tests will only generate positive results if contaminated undergarments are from vaginal fluids from a pregnant female.

Equipment for home testing can encompass a small microscope. Hom emicroscopes are convenient to use, cost effective, and essential for interpretation of certain cell staining techniques. Color tests combined with TLC can be made very compact and easy to use. Typical testing can take only 10–30 minutes for a typical TLC analysis (with colorization). Equipment for these types of tests can be supplied in a small kit. Spot tests for occult blood and indoles can be performed in a very short amount of time. A "Dot Blot" DNA test requires only a minimum of sample preparation and manipulation.

At home DNA testing can be accomplished when all reagents and DNA primers are provided to identify male and female chromosomes markers. A simple home DNA test kit can contain multiple wells of nucleic bases and PCR enzymes. A dye can be added that allows a spectral shift in the color the DNA-dye complex when the target DNA fragment is present. This home test kit can contain all necessary materials to generate a positive DNA-dye signal when the appropriate male or female gene is present. This test kit is then collected to a small spectral monitor and appropriate digital signal capturing hardware and software to be monitored with a laptop computer. The increase in DNA signal following the DNA-PCR amplification will be monitored and it will fall within certain limits over a specified time period to eliminate false-positive finding. All these reagents, hardware, software, and visual display of the data greatly simplifies the criminal investigator in the field or the spouse at home who must reach a conclusion concerning sex crimes or infidelity in a mate.

In conclusion, there are a number of routes that can be taken to perform sex crime investigations or fidelity testing using undergarments contaminated with biochemicals or industrial hygiene products or spermicides. Samples can be collected and sent to a commercial laboratory for in-depth analyses where ultratrace levels of compounds are chemically fingerprinted with high precision. Comparisons of the data from unknown stains to libraries of standards can lead to conclusions with high confidence levels.

At-home testing can be problematic if the sample is dilute, handled by inexperienced individuals, or contaminated with house-hold chemicals (e.g., soap, bleach, whiteners, etc.). In cases of home-testing the analysis approach must also be easy for the lay-person to perform. For these types of investigations, conclusions can be reached with more certainty when more than one test is applied to the undergarments.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

I claim:

1. A method for determining the presence of chemicals or compounds indicative of a sexual encounter, comprising:

testing a sample taken from a garment of a male for the presence of at least one compound selected from a group consisting of acetic acid, pyridine, furfural, benzaldehyde, short chain fatty acid, 3hydroxybutanone, 2-piperidone, butyric acid, isovaleric acid, propionic acid, lactic acid and 1-pyrroline.

2. A method for determining the presence of chemicals or compounds indicative of a sexual encounter, comprising:

testing a sample for the presence a chemical or compound selected from a group consisting of a lubricant, and a spermicide.

3. A method for determining the presence of chemicals or compounds indicative of a sexual encounter, comprising:

testing a sample for the presence of a chemical or chemical selected from a group consisting of benzoic acid, carbopol 940, methyl paraben, propylene glycol, polyethylene glycol, methyl cellulose, xanthan gum, methyl paraben, pectin, propyl paraben, glycerine, hydroxyethyl cellulose, glucano delta lactone, chlorhexidine gluconate, polyquaternium, propyl paraben, benzalkonium chloride, nonoxynol-9, ascorbic acid and sodium carboxymethyl cellulose.

4. A method for determining the presence of chemicals or compounds indicative of a sexual encounter, comprising:

testing a sample for the presence of a vaginal compound, wherein certain compounds in vaginal fluid possess function groups that form specific color patterns when analyzed using thin layer chromatography (TLC), wherein the step of testing a sample for the presence of a vaginal compound comprises:

contacting said sample with a solvent;

analyzing said solvent with TLC to produce spots;

contacting said spots with colorizing reagents to obtain a unique pattern of colored spots; and overlaying said pattern with a transparent template that comprises a pattern that is specific to a particular vaginal compound, wherein a vaginal compound is indicated if said unique pattern of colored spots matches said pattern that is specific to a particular vaginal compound.

5. The method of claim 4, wherein said certain compounds comprise acid that reacts with bromophenyl blue to form yellow spots on a blue background, aldehyde that reacts with 2,4-dinitrophenylhydrazine and generate unique phenylhydrazone-colored products, amine that reacts with ninhydrin or o-phthaldehyde to form purple or fluorescent chromophores and tertiary amine that reacts with Dragendorff's reagent or iodoplatinate to form orange or dark brown colored spots.

6. A method for determining the presence of chemicals or compounds indicative of a sexual encounter, comprising:

testing a sample for the presence of an industrial chemical or compound, wherein the step of testing a sample for the presence of an industrial chemical or compound comprises:

contacting said sample with a solvent;

producing, from said solvent, a chromatograph on a thin layer chromatograph plate; and staining said plate with iodine vapor, wherein said iodine vapor will highlight an industrial chemical or compound.

7. The method of claim 6, wherein said iodine vapor will produce a characteristic brown-to-yellow color if Nonoxynol-9 is present.

8. A method for determining the presence of chemicals or compounds indicative of a sexual encounter, comprising:

testing a sample for the presence of at least one chemical signature-compound selected from the group consisting of (1) an oral-derived saliva compound, (2) blood, (3) a vaginal compound, (4) a compound derived from the lower colon (5) an industrial chemical or compound, and (6) material introduced into the vagina in association with feminine hygiene or sexual activity, wherein the presence of said at least one chemical signature-compound indicates a sexual encounter with another, further comprising testing a sample for the presence of lipstick, comprising:

contacting said sample with a solvent;

analyzing said solvent with TLC to produce at least one Rf value; and comparing said at least one $R_f$ value with a standard which shows $R_f$ values for particular components of lipstick, wherein said at least one $R_f$ value will match at least one $R_f$ value of said $R_f$ values for particular components of lipstick when lipstick is present.

* * * * *